United States Patent [19]

Sin et al.

[11] Patent Number: 5,643,571
[45] Date of Patent: Jul. 1, 1997

[54] METHOD FOR CONTROLLING INFECTIOUS DISEASES IN FISH AND OTHER AQUATIC LIFEFORMS IN A CLOSED CULTURE SYSTEM

[75] Inventors: Y. M. Sin; K. H. Ling; T. J. Lam, all of Singapore, Singapore

[73] Assignee: National University of Singapore, Singapore

[21] Appl. No.: 466,025

[22] Filed: Jun. 6, 1995

Related U.S. Application Data

[63] Continuation of Ser. No. 103,054, Aug. 9, 1993, abandoned, which is a continuation-in-part of Ser. No. 929,865, Aug. 17, 1992, abandoned.

[51] Int. Cl.$^6$ ............ A61K 39/40; A61K 39/42; C07K 16/08; C07K 16/12
[52] U.S. Cl. .................. 424/159.1; 424/164.1; 530/390.1
[58] Field of Search ............ 424/130.1, 140.1, 424/184.1, 159.1, 164.1, 163.1; 530/387.1, 389.1, 389.4, 390.1, 389.5

[56] References Cited

U.S. PATENT DOCUMENTS

| 3,492,400 | 1/1970 | Klontz et al. | 424/92 |
| 4,309,416 | 1/1982 | Gratzek et al. | 424/88 |
| 5,064,645 | 11/1991 | Frechette et al. | 424/85.8 |

OTHER PUBLICATIONS

Sin, Y.M., Ling, K.H., Lam, T.J., 1992. Protection against velvet disease in goldfish recovered from ichthyophthiriasis. Aquaculture, 102; 187–191.

Ling, K.H., Sin, Y.M. and Lam, T.J., 1992. Studies on immune response in freshwater ornamental fish against ichythyophthirius multifiliis fouquet 1876. Singapore Journal of Primary Production, 20, 46–52.

Cross "A Review of Methods to Control Ichthyophthiriasis" Prog. Fish-culturist, 34, 1972, pp. 165–169.

Di Conza "Relationship of Catfish Serum Antibodies to Immunoglobulin in Mucus Secretions" Aust. Exp. Biol Med. Sci. 49, 1971, pp. 517–519.

Dickerson "tetrahymena Pyriformis as a Protective Antigen Against Ichthyophthirius Multifiliis Infection: Comparisons Between Isolates and Ciliary Preparations" J. Fish Biol. 24, 1984, pp. 523–528.

Ellis "Fish Vaccination" Academic Press, London 1988 pp. 1–19.

Gratzek "control and therapy of fish diseases" Adv. Vet. Sci. Comparat. Med. 27, 1983, pp. 297–324.

Goven "Protection of channel Catfish, Ictalurus Punctatus Refinesgue Against Ichthyophthirius Multifiliis Fouquet by Immunization" J. Fish Biol. 17, 1980, pp. 311–316.

Hines "Ichthyophthirius Multifiliis in the Mirror Carp, Cyprinus Carpio L" J. Fish Biol. 5, 1973, pp. 385–392.

Hines "Ichthyophthiriasis in the Mirror Carp Cyprinus Carpio L" J. Fish Biol 6, 1974, pp. 189–196.

Ingram "Substances Involved in the Natural Resistance of Fish to Infection –A Review" J. Fish Biol. 16, 1980, pp. 23–60.

Ling et al "A New Approach to Controlling Ichthyophthiriasis in a Closed Culture System of Freshwater Ornamental Fish" Journal of Fish Diseases, 14, 1991, pp. 595–598.

(List continued on next page.)

*Primary Examiner*—Christine M. Nucker
*Assistant Examiner*—Julie E. Reeves
*Attorney, Agent, or Firm*—Lowe, Price, LeBlanc & Becker

[57] ABSTRACT

A method for controlling infectious diseases in fish and other aquatic lifeforms, regardless of their developmental stage. The method of controlling pathogenic organisms detrimental to aquatic lifeforms includes steps of adding fish which are pre-immunized against one or more organisms pathogenic to fish to the same aquatic medium and with normal fish. The pre-immunized fish continuously and increasingly release antibodies against the pathogenic organisms into the same aquatic medium and can protect or prevent naive (normal, non-infected) fish or naive aquatic lifeforms from infection and are able to enhance the recovery of infected fish or any aquatic lifeforms infected with the same diseases.

18 Claims, 1 Drawing Sheet

OTHER PUBLICATIONS

Ourth "Secretory IGM, Lysozyme and Lymphocytes in the Skin Mucus of the Channel Catfish, Ictalurus Punctatus" Developmental and Comparative Immunology vol. 4, pp. 65–74, 1980.

Post "Textbook of fish Health" Revised and Expanded T.F.H. Publications, Inc. USA, 1987 pp. 159–223.

Sakai "Opsonization by Fish Antibody and Complement in the Immune Phagocytosis by Peritoneal Exudate Cells Isolated from Salmonid Fishes" Journal of Fish Diseases 7, 1984, pp. 29–38.

Sin et al "Protection Against Velvet Disease in Goldfish Recovered from Ichthyophthiriasis" Aquaculture, 102, 1992 pp. 187–191.

Ventura et al "Histopathology of Ichthyophthirius Multifiliis Infections in Fishes" Journal of Fish Biol. 27, 1985, pp. 185–203.

METHOD FOR CONTROLLING INFECTIOUS DISEASES IN FISH AND OTHER AQUATIC LIFEFORMS IN A CLOSED CULTURE SYSTEM

This application is a continuation of application Ser. No. 08/103,054 filed Aug. 9, 1993, now abandoned which is a continuation-in-part of of application Ser. No. 07/929,865 filed Aug. 17, 1992 now abandoned.

TECHNICAL FIELD

Infectious diseases cause heavy economic loss in intensive fish culture (Hines, R. S. et al., "Ichthyophthiriasis in the mirror carp *Cyprinus carpio*", III. *Pathology J. Fish Dis.* 6, (1973) 189–196). These may be due to the pathogenic parasites, bacteria, viruses or fungi. In Singapore, for example, the most important infectious disease in ornamental fish is due to *Ichthyophthirius multifiliis*. The protozoans (*I. multifiliis*) attack gills and skin and disturb the primary organs of excretion and osmoregulation in fish (Hines, R. S. et al., "Ichthyophthiriasis in the mirror carp *Cyprinus carpio*", III. *Pathology J. Fish Dis.* 6, (1973) 189–196; Ventura, M. T. et al., "Histopathology of *Ichthyophthirius multifiliis* infection in fishes", *J. Fish Dis.*, 27, (1985) 185–203). Various methods including physical-therapy and chemotherapy have been recommended for treating *I. multifiliis* infected fish when they are showing clinical signs of the disease (Cross, D. G., "A review of methods to control Ichthyophthiriasis", *Prog. Fish-culturist*, 34, (1972) 165–169; Gratzek, J. B., "Control and therapy of fish diseases", *Advances Vet. Sci. Comparat. Med.*, 27, (1983), 297–324; Post G. *Textbook of Fish Health*. (Revised and Expanded Edition), T. F. H. Publications Inc., USA, (1987)). However, all these methods can induce severe stress to the infected fish, thus rendering them more susceptible to infectious diseases subsequently. In addition, these methods are ineffective against the feeding stages of *I. multifiliis* which are associated with fish (Dickerson, H. W. et al., "*Tetrahymena pyriformia* as a protective antigen against *Ichthyophthirius multifiliis* infection: comparison between isolates and ciliary preparations", *J. Fish Biol.*, 24, (1984) 523–528). On the other hand, protection of channel catfish (Goven, B. A., et al., "Protection of channel catfish, *Ictalurus punctatus* Rafinesque, against *Ichthyophthirius multifiliis* Fouquet by immunization", *J. Fish Biol.*, 17, (1980) 311–316; Gratzek et al., U.S. Pat. No. 4,309,416, issued Jan. 5, 1982; Dickerson, H. W. et al., "*Tetrahymena pyriformia* as a protective antigen against *Ichthyophthirius multifiliis* infection: comparison between isolates and ciliary preparations", *J. Fish Biol.*, 24, (1984) 523–528) against *I. multifiliis* by immunization has been shown. Also effective protection by vaccination against bacteria (Klontz, U.S. Pat. No. 3,492, 400 issued Jan. 2, 1970) and viruses (Gratzek, J. B., "Control and therapy of fish diseases", *Advances Vet. Sci. Comparat. Med.*, 27, (1983), 297–324) have been reported in food fish. However, existing methods of administration of various vaccines are not fully practical on a mass scale. Methods of passive immunization involving injections of antibodies obtained from immunized individuals of a different species (Frechette et al., U.S. Pat. No. 5,064,645, issued Nov. 12, 1991) are also not fully practical on a large scale.

The present invention is a highly practical method wherein fish cultured in a closed recirculating system are continuously being protected against pathogens, such as protozoan parasites (e.g. Ichthyophthirius, Oodinium, Ichthyobodo, Trichodina, Chilodonella) and bacteria (e.g. Aeromonas) by one or more fish which are immunized against those pathogens and kept in the same recirculating system; these immunized fish release antibodies continuously to remove, or suppress the population of, the pathogens in the water and on/in the cultured lifeforms (if infected), and/or otherwise kill the pathogenic organisms.

SUMMARY OF THE INVENTION

A novel method of controlling pathogenic organisms in the aquatic environment and in fish and other aquatic lifeforms living in that environment, through placing in the same environment hardy fish immunized against those pathogenic organisms; these immunized fish continuously and increasingly release into the water antibodies against the pathogenic organisms concerned as long as the pathogenic organisms are still present in the water, thereby controlling the pathogenic organisms in the water and protecting the aquatic lifeforms concerned living in the same water against infection by the pathogenic organisms. In accordance with the present invention, fish may be immunized against one or more pathogenic organisms.

In the preferred embodiment for controlling pathogenic organisms in the aquatic environment, a closed culture system consisting of two (FIG. 1) or multi-tanks (FIG. 2) was used. All the tanks of this system are connected with PVC pipes with a pump and a filter so that water is continuously recirculating between the tanks. Hardy fish such as freshwater catfish or shubankin which were immunized against the pathogenic organisms such as Ichthyophthirius (causing white-spot disease), Oodinium (causing velvet disease), Ichthyobodo, Trichodina and Chilodonella (causing slimy skin) or Aeromonas (causing fin- and gill-rot disease) were kept in one tank while the remaining tanks were used to keep naive fish or fish infected by the pathogenic organisms concerned.

The method has demonstrated its effectiveness not only in maintaining naive fish free from infection but also in facilitating the rapid recovery of the infected fish. The protection was due to the antibodies in the aquatic environment released by the immunized hardy fish.

Although evidence for the effectiveness of the invention is provided only for the white-spot disease (due to the parasitic protozoan, Ichthyophthirius), velvet disease (due to Oodinium) slimy skin disease (caused by Ichthyobodo, Trichodina and Chilodonella), and the fin- and gill-rot disease (due to the bacteria, Aeromonas) in freshwater ornamental fish, the inventive concept is applicable to any disease (whether due to parasites, bacteria, viruses, or fungi) in any species of freshwater or marine life (whether finfish or shellfish, e.g. crustaceans, mollusks and echinoderms) at any developmental stage (whether eggs, larvae, fry, juveniles or adults).

DETAILED DESCRIPTION OF THE INVENTION

Figure 1:
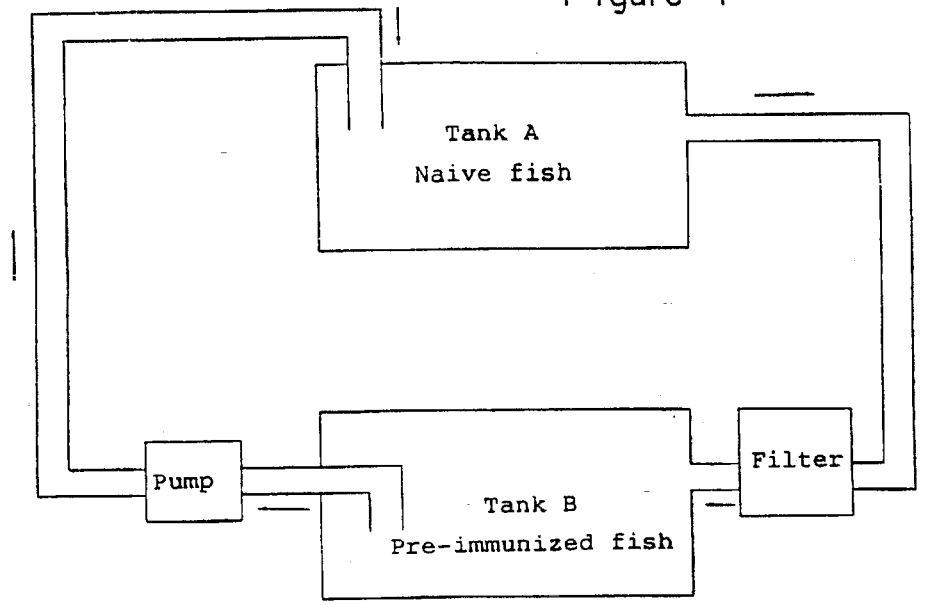
FIG. 1 is a side-view of a simple closed recirculating culture system. It consists of double deck aquarium tanks connected by PVC pipes with a pump and a filter. Water is continuously recirculating between the two tanks. The naive or infected fish (or other aquatic lifeforms) are kept in the upper tank while the immunized fish are placed in the lower tank. The lower tank is placed after the filter so that the water from the tank is pumped directing to the upper tank.

The inventive method described below provides a convenient, non-toxic, reliable and effective system of disease control in an aquatic environment by using immunized fish to release antibodies to control pathogenic organisms in the aquatic environment and in fish and other aquatic lifeforms (whether freshwater or marine) in a closed culture system.

In a preferred embodiment, various species of freshwater naive or infected ornamental fish have been repeatedly tested in the closed culture system as described above (FIG. 1 and 2) with freshwater hardy fish such as catfish and shubankin which were immunized against various types of pathogenic protozoans (causing white-spot disease, velvet disease, slimy skin disease) or bacteria (causing fin- and gill-rot disease) that commonly infect ornamental fish. Under such conditions, naive fish were protected from contracting the above diseases while the already infected fish showed rapid recovery from infection. The following examples demonstrate the efficacy of the inventive method.

Materials and Methods

Naive Fish:

Four species of ornamental fish were used: angel fish (*Pterophyllum altum*), weighing 2.5–3.5 g; black goldfish (*carassius auratus*), weighing 2.5–4.5 g; platy (*Xiphophorus maculatus*), weighing 1.5–2.2 g and tiger barb (*Capoeta tetrazona*), weighing 2.0–3.5 g. In addition, hardy naive fish such as catfish (*Clarias batrachus*) weighing 150–200 g and Shubankin (*Carassius auratus*) weighing 70–100 g, were used. Unless otherwise stated, all these fish were bred from healthy broodstocks and were not previously infected with *I. multifiliis* or any other obvious parasites. The fish were kept in well-aerated aged tap water at 28°–30° C., pH 6.5–7.2, dissolved oxygen between 6.0–7.8 ppm, and total hardness of water ($CaCO_3$) 72.5–80.3 mg/l. These fish were referred to as "naive or unprimed fish". All fish were fed commercial goldfish pellets and dried tubifex worms at 1% body weight per day.

*Ichthyophthirius Multifiliis*:

The parasites were originally isolated from goldfish from a local fish farm and maintained by regular introduction of naive fish into the tank. "Infected fish" used for experiments were obtained by exposing 5 naive ornamental fish to infectious free-swimming tomites (1000–1500 per fish) in a 1000 ml beaker for 1 hour before transferring to the tanks of the closed culture aquarium system.

Fish Immunized Against Protozoan Parasites (Example 1 to 4 and 6):

Catfish and Shubankin were injected intraperitoneally with 0.1 ml 0/85% NaCl solution containing $2.3 \times 10^6$ live tomites of *I. multifiliis*. For obtaining secondary immune response, a similar dose of live tomites was given via the same route 30 days after the initial injection. They were referred to as immunized fish.

Fish Immunized Against Bacteria (Example 5):

Catfish (*Clarias batrachus*) and Shubankin (*Carassius auratus*) were immunized by intraperitoneal injection of 0.2 ml 0.85% NaCl solution containing $3.2 \times 10^6$ formalin-killed *Aeromonas sp* which were collected from heavily infected tilapia and goldfish on day 0 and day 14. They were referred to as immunized fish.

Naive goldfish were infected 3 days after the exposure to the live *Aeromonas sp*. at a concentration of 3000/fish. Fish which were showing the clinical sign of the bacterial disease (fin and gill rot) were placed in the closed aquarium system.

Figure 2:
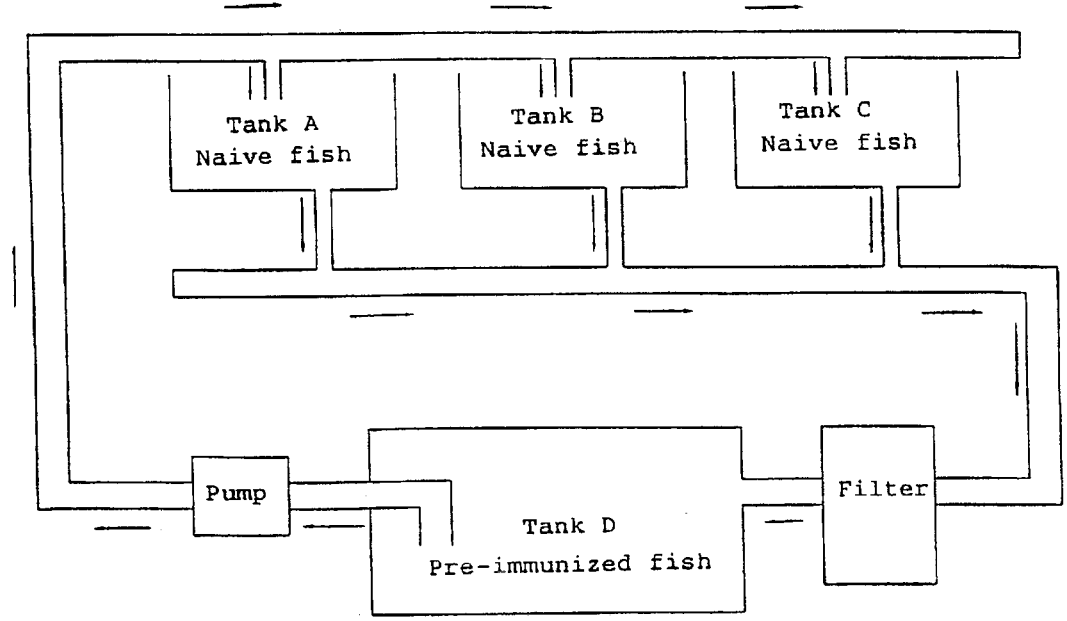
FIG. 2 is a side-view of a closed culture system which consists of more than two tanks. The main design is similar to that of FIG. 1. The lower tank D is used to keep immunized fish while the upper tanks (A to C) are used to keep naive or infected fish (or other aquatic species). Tanks A to C may be used to house naive or infected fish of different species separately.

Experiments:

All experiments were carried out in 20l glass tanks with constant aeration. No water renewal was carried out during the experimental period of 3 weeks to ensure that the fish were kept in an undisturbed environment. Fish were fed commercial goldfish pellets once a day. Unless otherwise stated, the immunized and infected fish were kept in separate tanks; the upper tank was used to keep naive or infected ornamental fish while the lower tank was used for keeping the immunized fish (FIG. 1). The number of pre-immunized, naive and infected fish per tank was varied according to the experimental design as stated in each table of results. FIG. 2 showed the same closed culture system but the number of upper tanks was increased to 3 for keeping more naive or infected ornamental fish.

Determination of Anti-multifiliis Antibodies:

Blood samples were collected by heparinized syringes and needles from the caudal vein of naive and immunized fish immediately before they were transferred into the separate tanks of the closed culture system. All sera were inactivated at 47° C. for 30 minutes (Sakai, D. K., "Opsonization by fish antibody and complement in the immune phagocytosis by peritoneal exudate cells isolated from salmonid fish", *J. Fish Dis.*, 7, (1984) 29–38) before being assayed by the modified method of immobilization as suggested by Hines et al. (Hines, R. S. et al., "Ichthyophthiriasis in the mirror carp *Cyprinus carpio*", IV. Physiological dystunction, *J. Fish Dis.*, 6, (1974) 365–371. Briefly, each serum was serially two-fold diluted with physiological saline in the cups of microtitrater plexiglass plates. About 10 to 15 active free-swimming tomites of *I. multifiliis* were introduced into each cup and the plates were gently shaken before being left in an air-conditioned room (23° C.) for 48 hours. The readings of the antibody activity that could immobilize *I. multifiliis* were carried out under the light microscope. The final endpoint for the antibody activity in each diluted serum was taken when 50% of the free swimming tomites became immobilized.

The antibody activity in mucus and aquarium water was also similarly determined. Fish mucus was obtained by swabbing 10 fish individually with a soft fine sponge into 100 ml of physiological saline. It was then filtered by a fine cheese cloth to remove fish scales and other solid particles. Levels of water antibody titres were measured 4 days after both immunized and infected fish had been introduced into the double-deck aquarium system. The number of free swimming tomites that became immobilized by the undiluted tank water was also determined.

As for Example 6, since the fish fry were far too small for collecting of blood samples for antibody titration, a modified method of immobilization testing on fish body fluid against the parasite was developed. This was done by random sampling of 3 fish fry from each of the system tank before the introduction of infective tomites, and 1 and 3 wks after the introduction of infective tomites. The fish fry were killed immediately and homogenized in a homogenizer according to their group, with 0.5 ml distilled water at 4° C. The homogenized body fluid was then separated by a microcentrifuge at 4° C. The supernatant was inactivated at 47° C. for 30 minutes (Sakai, D. K., "Opsonization by fish antibody and complement in the immune phagocytosis by peritoneal exudate cells isolated from salmonid fish", *J. Fish Dis.*, 7, (1984) 29–38) before being assayed by the modified method of immobilization as described above.

Statistical analysis:

All the data were analyzed using one-way analysis of variance followed by a Student-Newman-Keuls test. A value of $p < 0.05$ was considered to be significant.

Results:

In fish farms particularly quarantine and export centers where fish are stocked for export, the qualities of fish vary considerably because fish are obtained from different suppliers. Some fish may look healthy but may be subclinically infested with a low number of infectious parasites on their body and gill surface. Because of the netting, grading, transportation, water quality and crowding, these fish were usually vulnerable to diseases. It has been well established stress caused by the above factors can lower resistance of fish to infectious diseases (Gratzek, J. B., "Control and therapy of fish diseases", *Advances Vet. Sci. Comparat. Med.*, 27, (1983), 297–324). Although chemicals such as copper sulphate is widely used to treat ectoparasites on ornamental fish, this is not an ideal method because some species of fish are very sensitive to chemical treatment, rendering them more vulnerable to diseases subsequently. In Japan, no chemicals, except antibiotics, are allowed to treat infected culture food fish. In the U.S.A., a number of chemicals and drugs are also banned from use in aquaculture. Therefore, in order to cure infected fish and to control the outbreaks of infectious diseases, a more ideal method is to provide the aquatic environment with protective substances released from immunized fish continuously that can prevent the rapid multiplication of the disease organisms when the fish become weaker due to various stress factors.

We have shown that a significant number of infected fish recovered from infection in the presence of immunized fish (in the same tank) as compared to the controls, irrespective of species. Similar findings were also observed in the simple closed recirculating system (Example 1: Tables 1 and 2; FIGS. 1 and 2) where immunized fish were kept in a separate tank.

EXAMPLE 1

Tables 1 and 2 show the results obtained from the closed culture system which consisted of two aquarium tanks (FIG. 1). The upper tank contained 10 infected goldfish while the lower tank contained 1 immunized catfish (Table 1) or 2 pre-immunized shubankin (Table 2). The data in both tables clearly show that immunized fish provided a significant protection for the infected fish as compared to the controls. The data further show that immunized fish after secondary immune response provided a better protection of the infected fish than those after primary immune response.

TABLE 1

Control of Ich on 10 infected goldfish in the upper tank (FIG. 1) by using a catfish, which was pre-injected with 1 (primary immunization) or 2 (secondary immunization) doses of *I. multifiliis*, in the lower tank.

| Group (fish in lower tank) | n | No. of recovered[1] No. infected (upper tank) | Survival rate (%) |
| --- | --- | --- | --- |
| Control (no fish) | 9 | 25/90 | 28.89 |
| Control (naive catfish) | 3 | 7/30 | 23.33 |
| Test (immune catfish, 5 wk after 1st injection) | 3 | 21/30 | 70.00[a] |
| Test (immune catfish 1 wk after 2nd injection) | 3 | 26/30 | 86.67[b] |
| Test (immune fish, 2 wk after 2nd injection) | 3 | 27/30 | 90.00[c] | n = number of replicates.
[a]$p < 0.05$, [b]$p < 0.005$ and [c]$p < 0.001$ significantly different from both controls. Different superscripts indicate significant difference ($p < 0.05$) between test groups.
[1]Total of the replicates.

TABLE 2

Control of Ich on 10 infected goldfish in the upper tank (FIG. 1) by using 2 shubankin, which were pre-injected with 1 (primary immunization) or 2 (secondary immunization) doses of *I. multifiliis*, in the lower tank.

| Group (fish in lower tank) | n | No. of recovered[1] No. infected (upper tank) | Survival rate (%) |
| --- | --- | --- | --- |
| Control (no fish) | 12 | 33/120 | 27.50 |
| Control (naive shubankin) | 6 | 16/60 | 26.67 |
| Test (immune shubankin, 5 wk after 1st injection) | 6 | 41/60 | 68.33[a] |
| Test (immune shubankin 1 wk after 2nd injection) | 3 | 25/30 | 76.67[b] |
| Test (immune shubankin, 2 wk after 2nd injection) | 3 | 28/30 | 86.67[c] | n = number of replicates.
[a]$p < 0.05$, [b]$p < 0.005$ and [c]$p < 0.001$ significantly different from both controls. Different superscripts indicate significant difference ($p < 0.05$) between test groups.
[1]Total of the replicates.

EXAMPLE 2

It was shown that the higher the number of immunized fish (fish which had recovered from "ich" infection or after the pathogen injection) in relation to infected fish cultured in the same tank, the better was the recovery rate of the infected fish. (Ling, Sin and Lam, September 1991, *Journal of Fish Diseases*, Vol 14, p. 595–598; and Ling, Sin and Lam, March 1992, *Aquaculture*, Vol 102, p. 187–191, incorporated herein by reference). This indicates that the magnitude of response of the immunized fish against the parasites plays an important part in the protection of the infected fish. This view was further supported by the findings of Tables 3 and 4 that higher titres of anti-*I. multifiliis* antibodies were obtained in immunized fish after secondary immune response than those after primary immune response. Anti-*I. multifiliis* activity was also detected in the aquarium water 4 days after secondary-immunized fish were introduced into the lower tank. Although the activity in the tank water containing primary-immunized fish was only detected on day 12 based on 50% parasite immobilization test, it was detected on day 4 when the number of tomites immobilized by the tank water was counted instead of basing on 50% immobilization (Tables 5 and 6). This activity remained the same when the tank water was heated to 47° C. for 30 min, indicating they are not blood complements. However, the activity was lost when the tank water was heated to 100° C. for 30 minutes, suggesting that the protective substances are protein in nature. Since a significant increase in anti-*I. multifiliis* antibody activity was found in plasma, mucus and tank water after the secondary immunization of the hardy fish the protective substances in the water must be the antibodies released from the immunized fish through mucus. Although skin mucus was able to kill certain parasites was reported by Ingram, G. A., "Substances involved in the natural resistance of fish to infection—a review", *J. Fish Biol.*, 16, (1980) 23–60 and specific immunoglobulins were found in the mucus layer of some fish (Di Conza J. J. et al., "Relationship of catfish serum antibodies to immunoglobulin in mucus secretions", *Aust. J. Exp. Biol. Med. Sci.*, 49, (1971), 517–519; Ourth, D. D., "Secretory IgM, Lysozyme and lymphocytes in the skin mucus of the channel catfish, *Ictalurus Punctatus*", *Develop. Comp. Immunol.*, 4, (1980) 65–74) we are the first group to demonstrate that skin mucus of immunized fish could release antibodies into the water thereby producing effective protection against pathogens concerned for naive or infected fish.

TABLE 3

Anti-*I. multifiliis* antibody titres in serum, mucus and tank water of double-deck aquaria containing a catfish pre-injected with 1 or 2 doses of *I. multifiliis*.

| Group (catfish in lower tank) | n | Antibody titres ($-\log_2$) | | |
|---|---|---|---|---|
| | | Serum | Mucus | Tank Water |
| Control (naive fish) | 9 | 2.05 ± 0.43 | 0.00 ± 0.00 | 0.00 ± 0.00 |
| Test (1 wk after 1st injection) | 9 | 2.52 ± 0.87 | 0.00 ± 0.00 | 0.00 ± 0.00 |
| Test (3 wk after 1st injection) | 9 | 5.45 ± 0.65$^a$ | 1.65 ± 0.82$^d$ | 0.00 ± 0.00 |
| Test (5 wk after 1st injection) | 9 | 7.22 ± 0.45$^b$ | 3.15 ± 0.34$^e$ | 0.00 ± 0.00 |
| Test (1 wk after 2nd injection) | 9 | 9.16 ± 0.45$^c$ | 4.05 ± 0.46$^e$ | 0.13 ± 0.76$^g$ |

TABLE 3-continued

Anti-*I. multifiliis* antibody titres in serum, mucus and tank water of double-deck aquaria containing a catfish pre-injected with 1 or 2 doses of *I. multifiliis*.

| Group (catfish in lower tank) | n | Antibody titres ($-\log_2$) | | |
|---|---|---|---|---|
| | | Serum | Mucus | Tank Water |
| Test (2 wk after 2nd injection) | 9 | 11.87 ± 0.35$^c$ | 4.98 ± 0.72$^f$ | 0.95 ± 0.08$^h$ | n = number of replicates.
$^{a,d,g}p < 0.05$, $^{b,e,h}p < 0.005$ and $^{c,f}p < 0.001$ significantly different from their controls.
Different superscripts indicate significant difference (p < 0.05) between test groups.

TABLE 4

Anti-*I. multifiliis* antibody titres in serum, mucus and tank water of double-deck aquaria containing 2 shubankin pre-injected with 1 or 2 doses of *I. multifiliis*.

| Group (shubankin in lower tank) | n | Antibody titres ($-\log_2$) | | |
|---|---|---|---|---|
| | | Serum | Mucus | Tank Water |
| Control (naive fish) | 9 | 1.95 ± 0.63 | 0.00 ± 0.00 | 0.00 ± 0.00 |
| Test (1 wk after 1st injection) | 9 | 2.23 ± 0.76 | 0.00 ± 0.00 | 0.00 ± 0.00 |
| Test (3 wk after 1st injection) | 9 | 5.32 ± 0.45$^a$ | 1.25 ± 0.73$^d$ | 0.00 ± 0.00 |
| Test (5 wk after 1st injection) | 9 | 6.42 ± 0.78$^a$ | 2.97 ± 0.64$^d$ | 0.00 ± 0.00 |
| Test (1 wk after 2nd injection) | 9 | 8.25 ± 0.76$^b$ | 3.98 ± 0.45$^e$ | 0.00 ± 0.00 |
| Test (2 wk after 2nd injection) | 9 | 10.67 ± 0.66$^c$ | 4.65 ± 0.32$^f$ | 0.75 ± 0.56$^g$ | n = number of replicates.
$^{a,d,g}p < 0.05$, $^{b,e}p < 0.005$ and $^{c,f}p < 0.001$ significantly different from their controls.
Different superscripts indicate significant difference (p < 0.05) between test groups.

The anti-*I. multifiliis* antibody titres in sera and mucus of the immunized fish and in the tank water of the closed aquarium system were analyzed (Tables 9 and 10). The results show that the naive fish had a low anti-parasite antibody titre in their sera but this activity was absent in their mucus and in the tank water. On the contrary, catfish and shubankin at different weeks after immunization showed a significantly higher level of anti-parasite antibody in their sera and mucus as compared to the controls.

It has to be noted that anti-parasite antibody activity was also present in the aquarium water containing fish after primary immunization when the total number of immobilized tomites in the microtitration plates was counted (Tables 5 and 6). However, no such antibody activity was observed in the aquarium water containing the naive fish although the sera of these naive fish showed a low anti-parasite antibody activity. The antibody from the aquarium water containing immunized fish was still effective after heating to 47° C. for 30 minutes but completely lost when it was heated to 100° C. (Table 7).

TABLE 5

The, in vitro, immobilization activity of aquarium
tank water on active tomites of *I. multifiliis*.
The water was removed from the closed culture
system at different days after keeping the infected
fish in the upper tank and a immunized catfish in
the lower tank. The immunized catfish were pre-injected
with 1 or 2 doses of *I. multifiliis*.

| Group (catfish in lower tank) | No. of immobilized tomites (%) Days | | |
|---|---|---|---|
| | 4 | 8 | 12 |
| Control (naive fish) | 0.0 ± 0.0 | 0.0 ± 0.0 | 0.0 ± 0.0 |
| Test (1 wk after 1st injection) | 4.4 ± 1.8 | 5.6 ± 1.7 | 8.8 ± 2.0 |
| Test (3 wk after 1st injection) | 12.2 ± 2.2$^a$ | 23.3 ± 2.8$^b$ | 36.7 ± 3.3$^c$ |
| Test (5 wk after 1st injection) | 16.7 ± 2.3$^b$ | 26.6 ± 3.3$^b$ | 43.3 ± 2.3$^c$ |
| Test (1 wk after 2nd injection) | 35.5 ± 3.7$^c$ | 44.4 ± 4.1$^c$ | 54.4 ± 3.4$^d$ |
| Test (2 wk after 2nd injection) | 43.3 ± 4.1$^c$ | 51.1 ± 3.5$^d$ | 60.0 ± 2.3$^e$ |

$^{a,d}p < 0.05$, $^{b,e}p < 0.005$ and $^cp < 0.001$ significantly different from their controls.
Different superscripts indicate significant different ($p < 0.05$) between test groups.

TABLE 6

The, in vitro, immobilization of aquarium tank
water on active tomites of *I. multifiliis* as in
Table 5 except the lower tank containing 2
shubankin which were pre-injected with 1 or 2 doses
of *I. multifiliis*.

| Group (shubankin in lower tank) | No. of immobilized tomites (%) Days | | |
|---|---|---|---|
| | 4 | 8 | 12 |
| Control (naive fish) | 0.0 ± 0.0 | 0.0 ± 0.0 | 0.0 ± 0.0 |
| Test (1 wk after 1st injection) | 2.2 ± 1.4 | 3.3 ± 1.7 | 5.6 ± 1.8 |
| Test (3 wk after 1st injection) | 6.6 ± 1.7$^a$ | 16.7 ± 2.9$^b$ | 27.8 ± 2.8$^c$ |
| Test (5 wk after 1st injection) | 11.1 ± 2.0$^b$ | 21.1 ± 2.0$^b$ | 36.7 ± 2.3$^c$ |
| Test (1 wk after 2nd injection) | 30.0 ± 3.7$^c$ | 36.7 ± 3.3$^c$ | 46.7 ± 3.3$^d$ |
| Test (2 wk after 2nd injection) | 35.5 ± 3.4$^c$ | 42.2 ± 2.2$^d$ | 55.5 ± 1.7$^e$ |

$^{a,d}p < 0.05$, $^{b,e}p < 0.005$ and $^cp < 0.001$ significantly different from their controls.
Different superscripts indicate significant difference ($p < 0.05$) between test groups.

The above findings clearly demonstrate that antibodies are released into the aquatic environment by the immunized fish. It is without doubt that these substances not only kill the parasites or neutralize their toxins (if any) in the tank water but also removing parasites from the fish. The decrease of the parasites in the aquatic environment and on the fish body surface might allow the infected fish to have sufficient time to build up their active immunity.

EXAMPLE 3

Tables 8 and 9 show the effectiveness of the closed aquarium system (FIG. 2) when there were more tanks and more infected fish of different species. Pre-immunized fish may be in one or more tanks. The data again clearly demonstrate that a significantly greater number of infected fish recovered from infection with immunized fish in a separate tank as compared to the controls, irrespective of species. Hence, the present method must also work for various species of larger fish which were demonstrated to be infected by similar pathogenic protozoans (Hines, R. S. et al., "Ichthyophthiriasis in the mirror carp *Cyprinus carpio*", III. Pathology, *J. Fish Dis.*, 6, (1973) 189–196; Goven, B. A., et al., "Protection of channel catfish, *Ictalurus punctatus* Rafinesque, against *Ichthyophthirius multifiliis* Fouquet by immunization", *J. Fish Biol.*, 17, (1980) 311–316).

In the method of the present invention the pre-immunized fish and the naive or infected aquatic lifeforms may be in a flow-through method, where the number ratio of pre-immunized fish to fish to be protected is increased to a level compatible with producing sufficient substances effective against the specific pathogenic organisms. The pre-immunized fish and aquatic lifeforms to be protected may be, alternatively, in a floating net-cage. The pathogenic organisms to be controlled can be parasites, bacteria, viruses, fungi and can include mixtures of pathogenic organisms listed above.

Alternatively, the fish to be pre-immunized are species which tolerate injections of all kinds of vaccines and are able to respond by producing substantial amounts of substances effective against the pathogens concerned. The method of the present invention is applicable in hatcheries wherein the lifeforms to be protected are at a developmental stage that have an immature immune system.

In one embodiment of the invention the pre-immunized fish have been pre-immunized at least once with the pathogens concerned.

TABLE 7

Anti-*I. multifiliis* antibody activity of aquarium
water containing naive or immunized fish after heat
treatment. The immunized fish were pre-injected with
1 or 2 doses of *I. multifiliis*.

| Group | | Immobilization test of undiluted aquarium water* | | |
|---|---|---|---|---|
| (catfish in lower tank) | n | No heat treatment | 47° C. 30 min. | 100° C. 30 min. |
| Control (naive fish) | 12 | – | – | – |
| Test (1 wk after 1st injection) | 12 | – | – | – |
| Test (3 wk after 1st injection) | 12 | + | + | – |
| Test (5 wk after 1st injection) | 12 | + | + | – |
| Test | 12 | + | + | – |

TABLE 7-continued

Anti-*I. multifiliis* antibody activity of aquarium
water containing naive or immunized fish after heat
treatment. The immunized fish were pre-injected with
1 or 2 doses of *I. multifiliis*.

| Group | | Immobilization test of undiluted aquarium water* | | |
|---|---|---|---|---|
| (catfish in lower tank) | n | No heat treatment | 47° C. 30 min. | 100° C. 30 min. |
| (1 wk after 2nd injection) Test | 12 | + | + | − |
| (2 wk after 2nd injection) | | | | | n = number of replicates.
+: Tomites immobilized.
−: Motility of tomites not affected.
*: Determined on 7th day after fish being put into the closed aquarium system.

TABLE 8

Control of Ich on infected fish of different
species, 10 in each upper tank, by a immunized
catfish in the lower tank of the closed aquarium
system (FIG. 2). The immunized catfish used in
this experiment were at 2 wk after the second
injection of live tomites of *I. multifiliis*.

| | | Survival rate of infected fish (%) Lower tank containing | | |
|---|---|---|---|---|
| Infected Fish | n | No fish | Naive Fish | immunized fish** |
| Angelfish | 3 | 33.3 | 36.6 | 86.6 |
| Goldfish | 3 | 33.3 | 40.0 | 93.3 |
| Platy | 3 | 23.3 | 26.7 | 83.3 |
| Tiger barbs | 3 | 10.0 | 13.3 | 63.3 | n = number of replicates (total 90 fish).
**All significantly (p < 0.005) different from their controls.

TABLE 9

Control of Ich on infected fish, 10 in each upper
tank, by 2 immunized shubankin in the lower tank
of the closed aquarium system (FIG. 2). The immunized
shubankin were obtained at 2 wk after the second
injection of the live tomites of *I. multifiliis*.

| | | Survival rate of infected fish (%) Lower tank containing | | |
|---|---|---|---|---|
| Infected Fish | n | No fish | Naive Fish | immunized fish** |
| Angelfish | 3 | 33.3 | 30.0 | 83.3 |
| Goldfish | 3 | 30.0 | 26.6 | 86.7 |
| Platy | 3 | 20.0 | 23.3 | 80.0 |
| Tiger barbs | 3 | 3.3 | 6.7 | 56.7 | n = number of replicates (total 90 fish).
**significantly (p < 0.005) different from their controls.

EXAMPLE 4

The next two experiments were to test the method with ornamental fishes collected from two fish farms where the fishes were found to be carriers of some infectious diseases. Different numbers of the 3 species were kept in the closed aquarium system. The results in Tables 10 and 11 showed that significant protection was found when they were kept with the immunized fish. Fish in the controls died of white-spot (Ich) or velvet disease which was due to the spread of those protozoans from carrier fish. The ornamental fishes which were kept in the closed culture system with immunized fish remained healthy and free of parasitic protozoan diseases for a period of 6 months before the experiment was terminated.

This shows that the method does not provide a transient protection but that it lasts as long as the particular pathogens are still present in the water. The study also showed that fish from the above fish farm kept in the closed culture system with a secondary immunized catfish against *I. multifiliis* had a significantly higher survival rate towards other protozoan parasites (Ichthyopodo, Trichodina and Chilodonella) as compared to the controls (Table 12). Our studies also showed that fish recovered from "ich" exhibited effective protection against velvet disease. In addition, goldfish immunized with *I. multifiliis* developed protective immunity not only against *I. Multifiliis* but also towards other ecto-parasitic protozoans, such as *Ichthyobodo necatrix*, *Chilodonella cyprini*, and *Trichodina sp.*, which are commonly found in the tropics (Tables 13–17). The results also showed that the protection was correlated with the antibody titers in their plasma and skin mucus (Table 18).

TABLE 10

Control of Ich and velvet disease on ornamental
fish collected from fish farm A* in a closed
culture system using a secondary immunized catfish.
Each of the 3 upper tanks consisted of different
number of different species of ornamental fish.
The lower tank contained a catfish which was pre-
injected with 2 doses of *I. multifiliis*.

| | Survival Rate (%) No. of fish of each species used | | | | | |
|---|---|---|---|---|---|---|
| | Control | | | Test[1] | | |
| Fish** | 10 | 20 | 30 | 10 | 20 | 30 |
| Goldfish | 20 | 15 | 23.3 | 100 | 90 | 90 |
| Tiger barbs | 10 | 10 | 6.7 | 90 | 85 | 86.7 |
| Platy | 30 | 30 | 33.3 | 100 | 95 | 93.5 |

*Some fish were randomly chosen for parasite determination before putting them into the closed system: Tiger barbs were the carrier of *I. multifiliis* and *Oodinium pillularis* while goldfish were carrier of *Costia sp.* and *Gyrodactylus sp.*
**Each species placed separately in a tank.
[1]Significantly (p < 0.05) different from their control groups.

TABLE 11

Control of Ich on ornamental fish collected from
fish farm B* in a closed culture system using a
secondary immunized catfish against *I. multifiliis*.

| | Survival Rate (%) No. of fish of each species used | | | | | |
|---|---|---|---|---|---|---|
| | Control | | | Test[1] | | |
| Fish** | 10 | 20 | 30 | 10 | 20 | 30 |
| Goldfish | 20 | 30 | 30 | 90 | 100 | 92.3 |
| Tiger barbs | 30 | 25 | 26.3 | 100 | 90 | 96.6 |

TABLE 11-continued

Control of Ich on ornamental fish collected from fish farm B* in a closed culture system using a secondary immunized catfish against *I. multifiliis*.

|  | Survival Rate (%) No. of fish of each species used | | | | | |
|---|---|---|---|---|---|---|
|  | Control | | | Test[1] | | |
| Fish** | 10 | 20 | 30 | 10 | 20 | 30 |
| Platy | 20 | 10 | 10 | 90 | 85 | 86.6 |

*Platy were the carrier of *I. multifiliis* and *Tricodina sp.* Goldfish were the carrier of *Costia sp.* and *Tricodina sp.* Tiger barbs were the carrier of *Costia sp.* and *Gyrodactylus sp.*
**Each species placed separately in a tank.
[1]Significantly (p < 0.05) different from their control groups.

TABLE 12

Control of Chilodonella, Ichthyopodo, and Trichodina on ornamental fish collected from fish farm B in a closed culture system using a secondary immunized catfish against *I. multifiliis*.

|  | Survival Rate (%) | | | | | |
|---|---|---|---|---|---|---|
|  | Chilodonella | | Ichthyopodo | | Trichodina | |
| Fish** | Control | Test | Control | Test | Control | Test |
| Goldfish | 6.7 | 93.3 | 24.5 | 85.6 | 13.3 | 87.5 |
| Tiger barbs | 3.3 | 87.5 | 6.3 | 76.5 | 15.5 | 82.6 |
| Platy | 10 | 95.5 | 15.5 | 90.5 | 25.5 | 92.6 | n = 3 replicates (total 30 fish).
**Each species placed separately in a tank.
[1]Significantly (p < 0.05) different from their control groups.

EXAMPLE 5

Table 19 shows that immunized hardy fish when kept with the bacteria-infected goldfish showing fin- and gill-rot disease were able to facilitate the recovery of the latter. On the contrary, all the infected goldfish when kept with the naive hardy fish died within 14 days.

EXAMPLE 6

Tables 20 and 21 show the effectiveness of the closed aquarium system (FIG. 2) when there were more tanks and fish fry of different ornamental fish species were kept. The data again clearly demonstrate that a significantly higher protection on fry kept with the immunized catfish in a separate tank as compared to the controls, irrespective of species. Hence, the present method also works for younger stages (fry) of different ornamental fish species.

The above detailed examples (1 to 6) of the present invention demonstrate that the method provides a relatively pathogen-free closed aquatic environment for naive or infected ornamental fish in which pathogens are kept in check by antibodies released from hardy fish which have been immunized against those pathogens. This method is self-generating with antibodies continuously and increasingly being released by the immunized fish as long as the particular pathogens are still present in the water (a process known as secondary immune response). By this means, the antibodies constantly act as a preventive measure for the aquatic environment by removing, or suppressing the population of, pathogens in the water, thereby preventing infection or further infection or disease outbreak.

Furthermore, a variety of antibodies against various common infectious pathogens in a particular species of aquatic lifeform can be introduced into the aquatic environment at the same time by immunizing a small number of hardy fish with those vaccines. For instance, a few hardy fish can be immunized with a few vaccines of pathogenic protozoans, bacteria and viruses that commonly infect culture fish. Thus, antibodies against these pathogens will be released into the aquatic environment. This method is more effective and practical than by injecting heterologous antibodies into fish for passive immunity (Frechette et al., U.S. Pat. No. 5,064, 645, issued Nov. 12, 1991). The latter method would require repeated administration whereas the present invention is a self-generating system with antibodies continuously and increasingly being released by the immunized fish as long as the particular pathogens are still present in the water.

TABLE 13

Protection of naive and immunized goldfish against *I. multifiliis* challenge. The immunized fish had been treated twice with live tomites of *I. multifiliis* by immersion or injection.

| Group (treatment) | No. not infected Total no. challenged | Protection (%) | Mortality (%) |
|---|---|---|---|
| Control 1* (naive goldfish) | 2/90 | 2.2 | 97.7 |
| Test 1** (immersion) | 90/90 | 100.0[a] | 0.0[b] |
| Control 2* naive goldfish | 3/90 | 3.3 | 95.6 |
| Test 2** (injection) | 88/90 | 97.8[a] | 0.0[b] |

*Naive (control) goldfish had been injected with or immersed twice in saline prior to challenge.
**A very small number of these fish showed light infections.
[a]Percentage of protection is significantly (P < 0.05) different from controls.
[b]Percentage of mortality is significantly (P < 0.05) different from controls.

TABLE 14

Protection of naive and immunized goldfish against *O. pillularis* challenge. The immunized fish had been treated twice with live tomites of *I. multifiliis* by immersion or injection.

| Group (treatment) | No. not infected Total No. challenged | Protection (%) | Mortality (%) |
|---|---|---|---|
| Control 1* (naive goldfish) | 0/90 | 0.0 | 100.0 |
| Test 1** (immersion) | 70/90 | 77.7[a] | 11.1[b] |
| Control 2* naive goldfish | 1/90 | 1.1 | 100.0 |
| Test 2** (injection) | 66/90 | 73.3[a] | 13.3[b] |

*Naive (control) goldfish had been injected with or immersed twice in saline prior to challenge.
**A small number of these fish showed light infections.
[a]Percentage of protection is significantly (P < 0.05) different from their controls.
[b]Percentage of mortalities is significantly (P < 0.05) different from their controls.

TABLE 15

Protection of naive and immunized goldfish against Trichodina challenge. The immunized fish had been treated twice with live tomites of *I. multifiliis* by immersion or injection.

| Group (treatment) | No. not infected Total No. challenged | Protection (%) | Mortality (%) |
|---|---|---|---|
| Control 1* naive goldfish | 0/60 | 0.0 | 83.3 |
| Test 1** (immersion) | 46/60 | 76.7$^a$ | 8.3$^b$ |
| Control 2* naive goldfish | 2/60 | 3.3 | 86.7 |
| Test 2** (injection) | 42/60 | 70.0$^a$ | 13.3$^b$ |

*Naive (control) goldfish had been injected with or immersed twice in saline prior to challenge.
**A small number of these fish showed light infections.
$^a$Percentage of protection is significantly (P < 0.05) different from controls.
$^b$Percentage of mortality is significantly (P < 0.05) different from controls.

TABLE 16

Protection of naive and immunized goldfish against Ichthyobodo challenge. The immunized fish had been treated twice with live tomites of *I. multifiliis* by immersion or injection.

| Group (treatment) | No. not infected Total No. challenged | Protection (%) | Mortality (%) |
|---|---|---|---|
| Control 1* naive goldfish | 0/60 | 0.0 | 80.0 |
| Test 1** (immersion) | 45/60 | 75.0$^a$ | 8.3$^b$ |
| Control 2* naive goldfish | 1/60 | 1.7 | 75.0 |
| Test 2 a** (injection) | 44/60 | 73.3$^a$ | 5.0$^b$ |

*Naive (control) goldfish had been injected with or immersed twice in saline prior to challenge.
**A small number of these fish showed light infections.
$^a$Percentage of protection is significantly (P < 0.05) different from controls.
$^b$Percentage of mortality is significantly (P < 0.05) different from controls.

TABLE 17

Protection of naive and immunized goldfish against Chilodonella challenge. The immunized fish had been treated twice with live tomites of *I. multifiliis* by immersion or injection.

| Group (treatment) | No. not infected Total No. challenged | Protection (%) | Mortality (%) |
|---|---|---|---|
| Control 1* naive goldfish | 3/30 | 10.0 | 66.7 |
| Test 1** (immersion) | 28/30 | 93.3$^a$ | 0.0$^b$ |
| Control 2* naive goldfish | 5/30 | 16.7 | 83.3 |
| Test 2** (injection) | 27/30 | 90.0$^a$ | 3.3$^b$ |

TABLE 17-continued

Protection of naive and immunized goldfish against Chilodonella challenge. The immunized fish had been treated twice with live tomites of *I. multifiliis* by immersion or injection.

| Group (treatment) | No. not infected Total No. challenged | Protection (%) | Mortality (%) |
|---|---|---|---|

*Naive (control) goldfish had been injected with or immersed twice in saline prior to challenge.
**A small number of these fish showed light infections.
$^a$Percentage of protection is significantly (P < 0.05) different from controls.
$^b$Percentage of mortality is significantly (P < 0.05) different from controls.

TABLE 18

Serum and mucus antibody titres of naive and immunized goldfish which were Immunized twice by live tomites of *I. multifiliis* (immersion or injection) against different parasitic protozoans.

| Group (treatment) | Antibody titres ($-\log_2$) Control (Naive Fish) | | Test (immunized fish) | |
|---|---|---|---|---|
| | Mucus | Plasma | Mucus | Plasma |
| Anti-Ich.* (immersion) | 0.00 ± 0.00 | 2.11 ± 0.39 | 5.98 ± 0.65$^d$ | 10.65 ± 0.45$^a$ |
| Anti-Ich.* (injection) | 0.00 ± 0.00 | 2.00 ± 0.44 | 4.43 ± 0.81$^e$ | 11.11 ± 0.59$^a$ |
| Anti-Oodinium** (immersion) | 0.00 ± 0.00 | 2.22 ± 0.52 | 3.33 ± 0.67$^e$ | 5.62 ± 0.79$^c$ |
| Anti-Oodinium** (injection) | 0.00 ± 0.00 | 2.11 ± 0.39 | 3.05 ± 0.86$^e$ | 5.82 ± 0.43$^c$ |
| Anti-Trichodina* (immersion) | 0.11 ± 0.89 | 1.79 ± 0.51 | 3.98 ± 0.69$^e$ | 6.01 ± 0.67$^c$ |
| Anti-Trichodina* (injection) | 0.00 ± 0.00 | 2.00 ± 0.44 | 2.87 ± 0.36$^f$ | 5.93 ± 1.15$^c$ |
| Anti-Ichthyobodo* (immersion) | 0.00 ± 0.00 | 2.11 ± 0.39 | 2.69 ± 0.83$^f$ | 5.33 ± 0.47$^c$ |
| Anti-Ichthyobodo* (injection) | 0.00 ± 0.00 | 2.33 ± 0.52 | 2.22 ± 0.81$^f$ | 5.01 ± 0.43$^c$ |
| Anti-Chilodonella* (immersion) | 0.11 ± 0.89 | 2.00 ± 0.44 | 4.22 ± 0.88$^e$ | 9.67 ± 0.81$^b$ |
| Anti-Chilodonella* (injection) | 0.00 ± 0.00 | 1.79 ± 0.51 | 3.52 ± 0.33$^e$ | 8.56 ± 0.88$^b$ |

*: Immobilization test; **: Inhibition of division.
$^{a,d}$: P < 0.005, $^{b,e}$p < 0.01 and $^{c,f}$p < 0.05: significantly different from controls.
Different superscripts indicate significantly (p < 0.05) different between test groups.

TABLE 19

Control of fin rot caused by *Aeromonas hydrophila* in goldfish by catfish or shubankin immunized with formalin-killed *A. hydrophila* on day 0 and 14. Two weeks after the 2nd injection, immunized fish were placed in the closed culture system.

| Group (fish in lower tank) | n | No. of recovered No. of infected | Survival rate (%) |
|---|---|---|---|
| Control 1 (no fish) | 3 | 0/30 | 0 |
| Control 2 (naive | 3 | 0/30 | 0 |

TABLE 19-continued

Control of fin rot caused by *Aeromonas hydrophila* in goldfish by catfish or shubankin immunized with formalin-killed *A. hydrophila* on day 0 and 14. Two weeks after the 2nd injection, immunized fish were placed in the closed culture system.

| Group (fish in lower tank) | n | No. of recovered No. of infected | Survival rate (%) |
|---|---|---|---|
| catfish) Test 1 (immunized catfish) | 3 | 25/30 | 83.3[a] |
| Test 2 (immunized shubankin) | 3 | 22/30 | 73.3[b] | n = number of replicates.
[a,b] $p < 0.005$ significantly different from the controls.

TABLE 20

Control of Ichthyophthiriasis in goldfish fry in a closed recirculation system by using secondary immunized catfish.

| Group (treatment) | No. not infected Total no. challenged | No. of recovered No. of infected | Average Survival rate (%) | Total Protection (%) |
|---|---|---|---|---|
| I Control 1* (no fish in lower tank) | 0/270 | 18/270 | 6.7 | 6.7 |
| II Control 2* (naive catfish in lower tank) | 3/270 | 22/267 | 8.2 | 9.3 |
| III** (immunized catfish in lower tank) | 118/270 | 96/152 | 63.2[a] | 79.3[b] |

*Inflicted of heavy infection of *I. multifiliis*.
**About half of the naive goldfish fry showed light infection.
[a]Percentage of survival is significantly ($P < 0.005$) different from the controls.
[b]Percentage of total protection is significantly ($P < 0.005$) higher from the controls.

TABLE 21

Control of Ichthyophthiriasis in guppy and platy fry in a closed recirculation system by using secondary immunized catfish.

| Group (treatment) | No. not infected Total no. challenged | No. recovered No. infected | Average Survival (%) | Total Protection (%) |
|---|---|---|---|---|
| I (guppy) Control 1 (no fish in lower tank) | 2/180 | 33/178 | 18.5 | 19.4 |
| II (guppy)* Control 2 (naive catfish in lower tank) | 3/180 | 35/267 | 19.4 | 21.1 |
| III (guppy)** (immunized | 96/180 | 63/84 | 75.0[a] | 88.3[b] |

TABLE 21-continued

Control of Ichthyophthiriasis in guppy and platy fry in a closed recirculation system by using secondary immunized catfish.

| Group (treatment) | No. not infected Total no. challenged | No. recovered No. infected | Average Survival (%) | Total Protection (%) |
|---|---|---|---|---|
| catfish in lower tank) IV (platy)* Control 1 (no fish in lower tank) | 0/90 | 8/90 | 8.9 | 8.9 |
| V (platy)* Control 2 (naive catfish in lower tank) | 0/90 | 10/90 | 11.1 | 11.1 |
| VI (platy)** (immunized catfish in lower tank) | 42/90 | 29/48 | 60.4[a] | 78.9[b] |

*Inflicted of heavy infection of *I. multifiliis*.
**About half of the naive fish showed light infection.
[a]Percentage of survival is significantly ($P < 0.005$) different from the controls.
[b]Percentage of total protection is significantly ($P < 0.005$) higher from the controls.

Further Applications of the Inventive Concept

Although we have tested the invention for the control of some protozoan diseases and one bacterial disease in freshwater fishes, the inventive concept can be applied for the control of any disease (whether due to parasites, bacteria, viruses or fungi) in any aquatic species (whether freshwater or marine and finfish or shellfish such as crustaceans and mollusks, or other lifeforms). The method to be applied to any aquatic species for the control of any disease will be the same as described above. Let us take the example of species A, which may be any species of crustacean, mollusk, fish, or any other aquatic lifeform (e.g. sea urchins), whether freshwater or marine, and whether eggs, larvae, fry, juveniles or adults. If we know the pathogens causing diseases in species A and can obtain the corresponding vaccines or the isolates to prepare the vaccines by available methods, the vaccines can be injected into any species of fish known to be hardy and to show good immune response, preferably with a good capacity to produce mucus that live in the same type of environment (i.e. freshwater or marine) as species A. At least two injections, spaced 14 to 30 days apart, are recommended to ensure a good secondary immune response. These fish will develop antibodies against the pathogens concerned (even if these pathogens of species A are not normally pathogenic to fish. Anyhow, the fish will produce an immune response as long as these pathogens are antigens to the fish).

These immunized fish are then kept with species A either in the same enclosure or in a separate enclosure but connected with the enclosure of species A in terms of the water flow. The immunized fish release antibodies into the water, and as long as the immunized fish continue to encounter the pathogens concerned in the water they will develop and release an increasing amount of antibodies into the water, thereby preventing infection/further infection and outbreak of the disease(s) in species A, and even causing rapid recovery in diseased individuals of species A.

The general principle is that any organism which causes a disease in any aquatic species of any stage of development, may be prepared as a vaccine for injection into hardy fish selected for this purpose even though the organism may not be pathogenic in the fish itself. As a foreign body, the organism-derived vaccine will elicit an immune response in fish thereby causing the production of antibodies which are released into aquatic environment continuously and in increasing quantities as long as the pathogen is still present in the water. These antibodies in the water will protect against infection and disease outbreak in that particular species.

It is to be noted that the inventive method is to make use of the immunized hardy fish, and not the cultured shellfish or other aquatic species, to produce and release protective antibodies, into the aquatic environment, to kill the particular pathogens in the water or those infecting the cultured lifeforms. Therefore, the inventive method can be used to control diseases in not only fish but also other aquatic lifeforms regardless of the species, size or developmental stage. The immunized fish are chosen as the source of antibodies because fish have been shown to produce protective humoral and cell-mediated immune response towards various aquatic disease-causing organisms such as *Aeromonas hydrophila, Edwardsiella ictaluri, Infectious pancreatic necrosis, Vibrio sp* and many others (Ellis, A. E., *Fish Vaccination.* Academic Press, London (1988)). Even if the pathogens that infect crustaceans, mollusks, echinoderms and other aquatic lifeforms are antigenically different from fish pathogens, the immune system of fish can still respond to the pathogens, and therefore the immunized fish can still be used as the source of antibodies for release into the water for protecting the said aquatic lifeform against the pathogens. At the minimum, the inventive concept can be used to effectively reduce or eliminate pathogenic organisms in the aquatic medium through placing in the medium appropriate fish which have been immunized against those pathogenic organisms.

In conclusion, the results of our experiments demonstrate that immunized hardy fish such as catfish and shubankin in a closed system of culture with infected fish are effectively enhancing the recovery of the latter, irrespective of species. The data also strongly evidence that the protection is due to a high level of anti-*I. multifiliis* antibodies present in the mucus of immunized fish which is released into the circulating water. The anti-*I. multifiliis* antibody activity was shown to protect fish not only from "Ich" but also against Oodinium and other protozoans, such as Ichthyobodo, Trichodina and Chilodonella. Since the 3 species of ornamental fish kept in this system with a immunized catfish were free of infectious protozoan diseases for a period of 6 months before the experiments were terminated despite some fish being carriers of infectious protozoa (Tables 10 and 11), the method is also effective in controlling the spread of the infectious organisms as long as needed. The method works equally well with a bacterial disease as shown in Table 19 and also prove to be very effective for the protection of fry of different species of ornamental fish against infectious parasitic diseases (Tables 8 and 9). All these data so far obtained have demonstrated that the immunized fish in a closed culture system is highly effective in protecting naive fish against infectious disease-causing organisms as well as facilitating the recovery of infected fish. Hence, it should work for any infectious disease, be it parasitic, bacterial, viral or fungal.

Although the efficacy of the present inventive method has been repeatedly tested only in ornamental fish, the inventive concept is applicable to other fish species as well as crustaceans, mollusks and other aquatic lifeforms (e.g. echinoderms), whether freshwater or marine and irrespective of the developmental stage and size. This is based on the following facts:

(1) Fish can produce protective substances (antibodies) against various vaccines prepared from pathogenic organisms, even those which are not pathogenic in the fish themselves (prior art, see references)

(2) The immunized fish can release the protective substances into the water (present invention).

(3) The immunized fish will continuously and increasingly release protective substances into the water as long as the pathogenic organisms are still encountered (present invention).

(4) The released protective substances can kill the pathogenic organisms in the water, thus removing them from the water (present invention).

(5) The released protective substances can even effect recovery of infected individuals (present invention).

It will be understood that the present invention is not limited to the method described but includes all modifications and variations that may come within the scope of the appended claims.

We claim:

1. A method of controlling one or more pathogenic organisms selected from the group consisting of protozoan parasites and bacteria wherein the pathogenic organisms are detrimental to aquatic lifeforms selected from the group consisting of fish, crustaceans, mollusks and echinoderms wherein the method comprises;
   a) adding immunized fish immunized against one or more of said pathogenic organisms to a culture system comprising an aquatic medium;
   b) permitting said immunized fish to release antibodies against the pathogenic organisms into the aquatic medium;
   c) providing the aquatic lifeforms to the aquatic medium wherein the aquatic lifeforms are to be treated or protected; and
   d) allowing the antibodies to immunoreact with the pathogenic organisms, thereby controlling the pathogenic organisms.

2. The method of claim 1, wherein the immunized fish have been injected at least once or twice with pathogenic organisms selected from the group consisting of Ichthyophthirius, causing white-spot disease, Oodinium, causing velvet disease, Ichthyobodo, Trichodina and Chilodonella, causing slimy skin, and Aeromonas, causing fin-rot and gill-rot disease.

3. The method of claim 1, wherein the culture system comprising a closed recirculation culture system incorporating a tank containing the immunized fish.

4. The method of claim 1, wherein the immunized fish are in one tank and the aquatic lifeforms are contained in one or more tanks connected to the tank containing the immunized fish and wherein the aquatic medium in the tank containing the immunized fish is recirculated between the one or more tanks containing the aquatic lifeforms.

5. The method of claim 1, wherein the immunized fish are in a flow-through tank with the aquatic lifeforms, and wherein the number ratio of immunized fish to aquatic lifeforms to be protected is sufficient to provide an effective amount of antibodies protective against the pathogenic organisms.

6. The method of claim 1, wherein the immunized fish and aquatic lifeforms are in a floating net-cage.

7. The method of claim 1, wherein the immunized fish are species which tolerate injections and are capable of producing body mucus containing antibodies which are effective against pathogenic organisms.

8. The method of claim 1, wherein the immunized fish and the aquatic lifeforms are both freshwater organisms.

9. The method of claim 1, wherein the immunized fish and aquatic lifeforms are both marine organisms.

10. The method of claim 1, wherein the aquatic lifeforms are at any stage of development.

11. The method of claim 8, wherein the aquatic lifeforms to be protected are non-infected.

12. The method of claim 1, wherein the aquatic medium is a component of a quarantine system for treating the aquatic lifeforms before culture or export.

13. The method of claim 10, wherein the aquatic medium is a component of a hatchery.

14. The method of claim 1, wherein the immunized fish are selected from the group consisting of catfish and shubankin.

15. The method of claim 14, wherein the aquatic lifeforms are selected from the group consisting of freshwater angel fish, goldfish, platy, and tiger barb.

16. The method of claim 15, wherein pathogenic organisms are selected from the group consisting of protozoans and bacteria wherein the protozoans cause white-spot disease, velvet disease and slimy skin disease, and wherein the bacteria cause fin-rot or gill-rot disease.

17. The method of claim 1, wherein the culture system is one or more selected from the group consisting of a closed recirculation system, a flow-through system, a floating net-cage, a pond system, a hatchery, a grow-out system, a tank, a holding tank and a quarantine tank.

18. The method of claim 3, wherein the immunized fish and the aquatic lifeforms are in the same tank in the closed recirculating culture system.

* * * * *